(12) United States Patent
Tsuruta

(10) Patent No.: US 12,226,259 B2
(45) Date of Patent: Feb. 18, 2025

(54) ULTRASOUND IMAGING SYSTEM, OPERATION METHOD OF ULTRASOUND IMAGING SYSTEM, AND COMPUTER-READABLE RECORDING MEDIUM

(71) Applicant: OLYMPUS CORPORATION, Tokyo (JP)

(72) Inventor: Teppei Tsuruta, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 393 days.

(21) Appl. No.: 17/225,230

(22) Filed: Apr. 8, 2021

(65) Prior Publication Data

US 2021/0236091 A1 Aug. 5, 2021

Related U.S. Application Data

(63) Continuation of application No. PCT/JP2018/038557, filed on Oct. 16, 2018.

(51) Int. Cl.
*A61B 8/00* (2006.01)
*A61B 8/12* (2006.01)

(52) U.S. Cl.
CPC .............. *A61B 8/466* (2013.01); *A61B 8/12* (2013.01); *A61B 8/463* (2013.01)

(58) Field of Classification Search
CPC ............ A61B 8/466; A61B 8/12; A61B 8/463
See application file for complete search history.

(56) References Cited

U.S. PATENT DOCUMENTS

2002/0035329 A1\* 3/2002 Kamiyama ............ A61B 8/461
600/458
2004/0242987 A1\* 12/2004 Liew .................... A61B 8/5223
600/407
(Continued)

FOREIGN PATENT DOCUMENTS

JP 2004-113628 A 4/2004
JP 2005-192900 A 7/2005
(Continued)

OTHER PUBLICATIONS

International Search Report dated Dec. 11, 2018 issued in PCT/JP2018/038557.

*Primary Examiner* — Rochelle D Turchen
(74) *Attorney, Agent, or Firm* — Scully, Scott, Murphy & Presser, P.C.

(57) ABSTRACT

An ultrasound imaging system includes an ultrasound imaging device configured to transmit and receive a signal based on transmission and reception of an ultrasound wave. The ultrasound imaging device includes a processor including hardware. The processor is configured to: generate a plurality of pieces of data of ultrasound images of an inside of a subject based on the signal, the ultrasound images being spatially separated from one another; invert a magnitude relationship of a luminance value of each of pixels in each of the ultrasound images; automatically set a first boundary across which the luminance value changes by a predetermined amount based on data of one of the ultrasound images; and automatically detect a second boundary in each of the ultrasound images based on the set first boundary.

19 Claims, 10 Drawing Sheets

(56) References Cited

U.S. PATENT DOCUMENTS

| | | | |
|---|---|---|---|
| 2005/0267366 A1* | 12/2005 | Murashita | G01S 15/8993 600/437 |
| 2010/0185094 A1 | 7/2010 | Hamada et al. | |
| 2013/0004047 A1 | 1/2013 | Shiki et al. | |
| 2019/0142528 A1* | 5/2019 | Vertikov | A61B 34/20 600/424 |
| 2020/0245968 A1* | 8/2020 | Nellur Prakash | G16H 50/20 |

FOREIGN PATENT DOCUMENTS

| | | | | |
|---|---|---|---|---|
| JP | 2005-342516 A | | 12/2005 | |
| JP | 2008-079821 A | | 4/2008 | |
| JP | 2010-167032 A | | 8/2010 | |
| JP | 2013-9832 A | | 1/2013 | |
| JP | 2015116201 | * | 6/2015 | A61B 8/00 |
| JP | 2015-231436 A | | 12/2015 | |

* cited by examiner

ULTRASOUND IMAGING SYSTEM, OPERATION METHOD OF ULTRASOUND IMAGING SYSTEM, AND COMPUTER-READABLE RECORDING MEDIUM

CROSS-REFERENCE TO RELATED APPLICATION

This application is a continuation of International Application No. PCT/JP2018/038557, filed on Oct. 16, 2018, the entire contents of which are incorporated herein by reference.

BACKGROUND

1. Technical Field

The present disclosure relates to an ultrasound imaging system, operation method of ultrasound imaging system, and computer-readable recording medium.

2. Related Art

In the related art, to observe characteristics of a subject, an ultrasound image that is generated using ultrasound waves has been used in some cases. The ultrasound image is generated by causing an ultrasound imaging device to perform image processing on an ultrasound signal that is received by an ultrasound transducer from living tissue.

In recent years, an external ultrasound imaging system that inverts a luminance value of an ultrasound signal to make it possible to easily view a blood vessel or the like having a low luminance value has been known (for example, see Japanese Laid-open Patent Publication No. 2008-79821, Japanese Laid-open Patent Publication No. 2005-192900, and Japanese Laid-open Patent Publication No. 2005-342516). In the external ultrasound imaging system, an ultrasound probe including the ultrasound transducer is brought into contact with a body surface of a subject and transmits and receives ultrasound waves.

SUMMARY

In some embodiments, an ultrasound imaging system includes an ultrasound imaging device configured to transmit and receive a signal based on transmission and reception of an ultrasound wave, the ultrasound imaging device including a processor including hardware. The processor is configured to: generate a plurality of pieces of data of ultrasound images of an inside of a subject based on the signal, the ultrasound images being spatially separated from one another; invert a magnitude relationship of a luminance value of each of pixels in each of the ultrasound images; automatically set a first boundary across which the luminance value changes by a predetermined amount based on data of one of the ultrasound images; and automatically detect a second boundary in each of the ultrasound images based on the set first boundary.

In some embodiments, an operation method of an ultrasound imaging system includes: generating a plurality of pieces of data of ultrasound images of an inside of a subject based on a signal depending on transmission and reception of an ultrasound wave, the ultrasound images being spatially separated from one another; inverting a magnitude relationship of a luminance value of each of pixels in each of the ultrasound images; automatically setting a first boundary across which the luminance value changes by a predetermined amount based on data of one of the ultrasound images; and automatically detecting a second boundary in each of the ultrasound images based on the set first boundary.

In some embodiments, provided is a non-transitory computer readable recording medium having an executable program stored thereon. The program causes an ultrasound imaging system to perform: generating a plurality of pieces of data of ultrasound images of an inside of a subject based on a signal depending on transmission and reception of an ultrasound wave, the ultrasound images being spatially separated from one another; inverting a magnitude relationship of a luminance value of each of pixels in each of the ultrasound images; automatically setting a first boundary across which the luminance value changes by a predetermined amount based on data of one of the ultrasound images; and automatically detecting a second boundary in each of the ultrasound images based on the set first boundary.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of an ultrasound imaging system according to the present disclosure will be described below with reference to the drawings. The present disclosure is not limited by the embodiments below. The present disclosure is applicable to a general ultrasound imaging system that includes an ultrasound endoscope in which an ultrasound transducer for transmitting and receiving ultrasound waves is arranged at a distal end of an insertion portion that is inserted into a subject.

Further, in the description of the drawings, the same or corresponding elements are appropriately denoted by the same reference symbols. Furthermore, it is necessary to note that the drawings are schematic, and dimensional relations among the components, ratios among the components, and the like may be different from the actual ones. Moreover, the drawings may include portions that have different dimensional relations or ratios.

Embodiment

Figure 1:
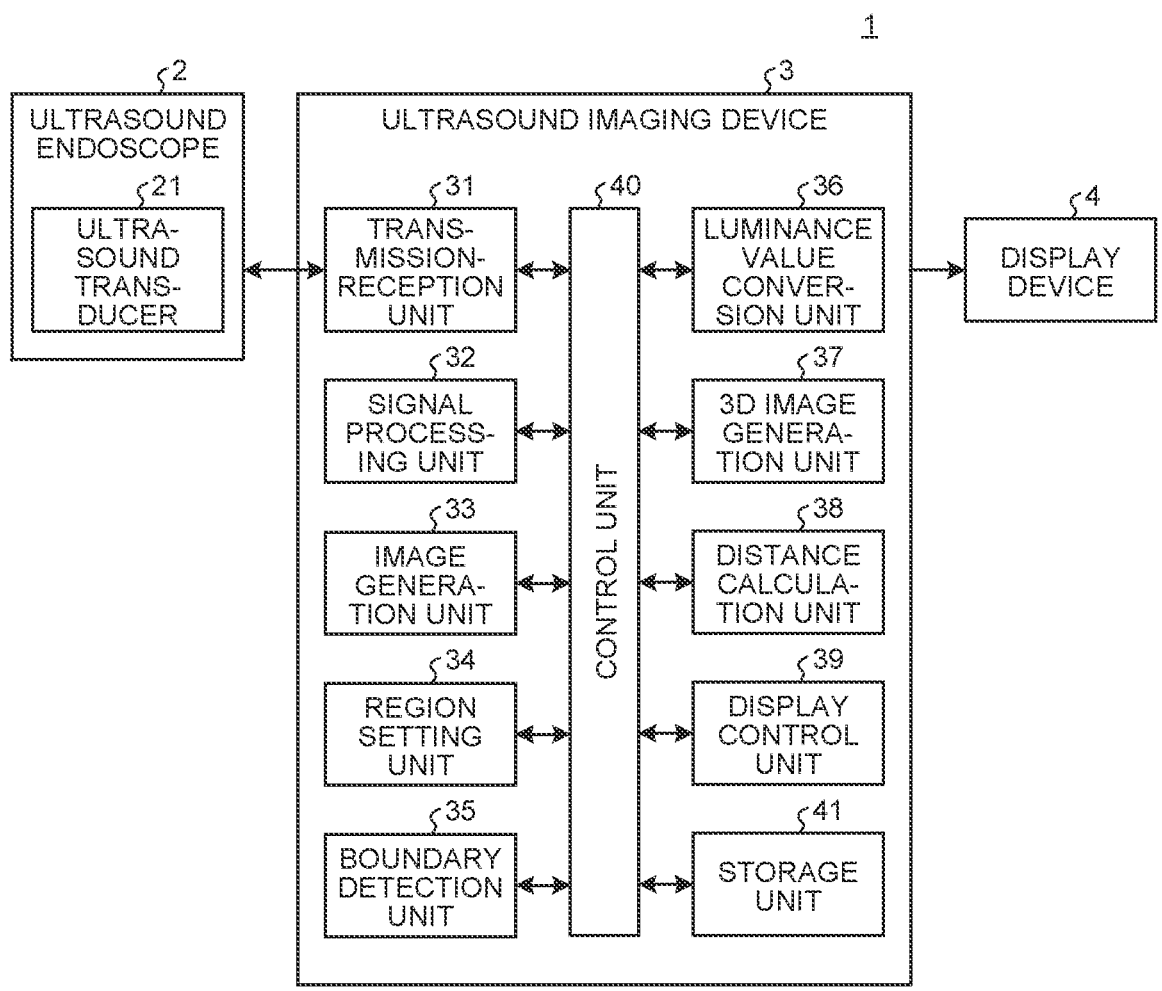
FIG. 1 is a block diagram illustrating a configuration of an ultrasound imaging system according to one embodiment of the present disclosure.

FIG. 1 is a block diagram illustrating a configuration of an ultrasound imaging system according to one embodiment of the present disclosure. As illustrated in FIG. 1, an ultrasound imaging system 1 includes an ultrasound endoscope 2 that transmits an ultrasound wave to a subject as an imaging target and receives an ultrasound wave reflected by the subject, an ultrasound imaging device 3 that generates an ultrasound image on the basis of an ultrasound signal acquired by the ultrasound endoscope 2, and a display device 4 that displays the ultrasound image generated by the ultrasound imaging device 3.

The ultrasound endoscope 2 includes an ultrasound transducer 21 that is arranged on a distal end of an insertion portion to be inserted into the subject and that transmits and receives an ultrasound wave. The ultrasound transducer 21 converts an electrical pulse signal received from the ultrasound imaging device 3 to an ultrasound pulse (acoustic pulse), applies the ultrasound pulse to the subject, converts an ultrasound echo reflected by the subject to an electrical echo signal (ultrasound signal) representing the ultrasound echo by a voltage change, and outputs the electrical echo signal. The ultrasound transducer 21 is, for example, a convex type, but may be a radial type or a linear type. Furthermore, the ultrasound endoscope 2 may cause the ultrasound transducer 21 to mechanically perform scanning, or may include, as the ultrasound transducer 21, a plurality of elements in an array manner and electronically perform scanning by electronically switching between the elements used for transmission and reception or delaying transmission or reception of each of the elements.

The ultrasound endoscope 2 generally includes an imaging unit that includes an imaging optical system and an image sensor, is inserted into a digestive tract (an esophagus, a stomach, a duodenum, or a large intestine) or a respiratory organ (a trachea or a bronchus) of the subject, and is able to capture an image of the digestive tract, the respiratory organ, or a peripheral organ (a pancreas, a gallbladder, a bile duct, a biliary tract, lymph nodes, a mediastinal organ, a blood vessel, or the like). Further, the ultrasound endoscope 2 includes a light guide that guides illumination light to be applied to the subject at the time of imaging. A distal end portion of the light guide reaches a distal end of the insertion portion of the ultrasound endoscope 2 to be inserted into the subject, and a proximal end portion of the light guide is connected to a light source device that generates the illumination light. Meanwhile, the ultrasound endoscope 2 may be configured without including the imaging unit.

The ultrasound imaging device 3 includes a transmission-reception unit 31, a signal processing unit 32, an image generation unit 33, a region setting unit 34, a boundary detection unit 35, a luminance value conversion unit 36, a three-dimensional image generation unit (hereinafter, described as a "3D image generation unit") 37, a distance calculation unit 38, a display control unit 39, a control unit 40, and a storage unit 41.

The transmission-reception unit 31 transmits and receives an electrical signal to and from the imaging unit and the ultrasound transducer 21. The transmission-reception unit 31 is electrically connected to the imaging unit, transmits image information, such as an imaging timing, to the imaging unit, and receives an imaging signal generated by the imaging unit. Further, the transmission-reception unit 31 is electrically connected to the ultrasound transducer 21, transmits an electrical pulse signal to the ultrasound transducer 21, and receives an echo signal that is an electrical reception signal from the ultrasound transducer 21. Specifically, the transmission-reception unit 31 generates an electrical pulse signal on the basis of a waveform and a transmission timing that are set in advance, and transmits the generated pulse signal to the ultrasound transducer 21.

The transmission-reception unit 31 amplifies the echo signal. The transmission-reception unit 31 performs sensitivity time control (STC) correction in which an echo signal with a larger reception depth is amplified with a higher amplification factor. Meanwhile, the depth corresponds to a distance of each of pixels in the ultrasound image from the ultrasound transducer 21. The transmission-reception unit 31 performs a process, such as filtering, on the amplified echo signal, generates a digital high-frequency (radio frequency (RF)) signal (hereinafter, also referred to as RF data) in a time domain by performing analog-to-digital (A/D) conversion, and outputs the RF data.

The signal processing unit 32 generates digital B-mode reception data on the basis of the RF data received from the transmission-reception unit 31. Specifically, the signal processing unit 32 performs a well-known process, such as a bandpass filtering, envelope detection, or logarithmic transformation, on the RF data, and generates the digital B-mode reception data. In the logarithmic transformation, a common logarithm of an amount obtained by dividing the RF data by a reference voltage is obtained, and represented by a decibel value. The signal processing unit 32 outputs the generated B-mode reception data to the image generation unit 33. The signal processing unit 32 is implemented by using a central processing unit (CPU), various arithmetic circuit, or the like.

The image generation unit 33 generates data of the ultrasound image on the basis of the B-mode reception data received from the signal processing unit 32. The ultrasound image is a cross-sectional image obtained by capturing an image of a cross section perpendicular to a longitudinal direction of the insertion portion of the ultrasound endoscope 2. The image generation unit 33 performs image processing, such as a gain process or a contrast process, using a well-known technique on the B-mode reception data, and generates B-mode image data that is the data of the ultrasound image by performing data decimation or the like in accordance with a data step width that is determined depending on a display range of the image on the display device 4. A B-mode image is a grayscale image in which values of red (R), green (G), and blue (B), which are variables used when an RGB color system is adopted as a color space, are equalized. In the ultrasound image, the value of RGB corresponds to a luminance value, where a portion with a large luminance value is represented by white and a portion with a small luminance value is represented by black.

The image generation unit 33 generates the B-mode image data by first performing, on the B-mode reception data obtained from the signal processing unit 32, a coordinate transformation for rearrangement such that a scanning range can be spatially correctly represented, and subsequently performing an interpolation process between pieces of the B-mode reception data to fill void between the pieces of the B-mode reception data.

Further, the image generation unit 33 generates data of a two-dimensional cross-sectional image of an arbitrary cross-section in the three-dimensional ultrasound image generated by the 3D image generation unit 37. The image generation unit 33 is implemented by using a CPU, various arithmetic circuits, or the like.

The region setting unit 34 sets a first region of interest and a second region of interest (which are to be described later) in a representative image that is selected by a user from an ultrasound image group including the ultrasound images. The region setting unit 34 is implemented by using a CPU, various arithmetic circuits, or the like.

The boundary detection unit 35 detects a boundary between the first region of interest and an external portion and a boundary between the first region of interest and the second region of interest. The boundary detection unit 35 is implemented by using a CPU, various arithmetic circuits, or the like.

The luminance value conversion unit 36 inverts a magnitude relationship of the luminance value of each of the pixels in the ultrasound image. Further, the luminance value conversion unit 36 sets a luminance value whose magnitude relationship has been inverted and that is equal to or smaller than a threshold to zero. Specifically, the luminance value conversion unit 36 performs a negative-to-positive conversion for inverting the magnitude relationship of the luminance value of each of the pixels in the ultrasound image, and sets a luminance value in a portion in which the luminance value is equal to or smaller than the threshold in the converted image to zero. Meanwhile, setting the luminance value to zero corresponds to deletion of an image of the corresponding portion in the ultrasound image. Furthermore, it is sufficient for the luminance value conversion unit 36 to appropriately invert the magnitude relationship of the luminance value of each of the pixels in the ultrasound image, and it may be possible to perform weighting such that a difference in the luminance value is more clearly reflected in a difference in brightness on the screen on a low luminance value side, and then invert the magnitude relationship of the luminance value. The luminance value conversion unit 36 is implemented by using a CPU, various arithmetic circuits, or the like.

The 3D image generation unit 37 generates data of the three-dimensional ultrasound image by synthesizing ultrasound images. The 3D image generation unit 37 is implemented by using a CPU, various arithmetic circuits, or the like.

The distance calculation unit 38 calculates a distance between two points that are specified in the subject displayed on the display device 4. The distance calculation unit 38 is implemented by using a CPU, various arithmetic circuits, or the like.

The display control unit 39 causes the display device 4 to display the ultrasound image, the three-dimensional ultrasound image in which the ultrasound images are synthesized, or the three-dimensional ultrasound image in which the ultrasound images with the inverted magnitude relationships of luminance values are synthesized. Specifically, the display control unit 39 generates data of an endoscopic image based on an imaging signal, data of an ultrasound image corresponding to an electrical echo signal, and data of the three-dimensional ultrasound image that is obtained by synthesizing ultrasound images. Furthermore, the display control unit 39 superimposes various kinds of information on the data of the endoscopic image and the data of the ultrasound image, outputs the superimposed data, and controls display on the display device 4. The display control unit 39 is implemented by using a CPU, various arithmetic circuits, or the like.

The control unit 40 controls the entire ultrasound imaging system 1. The control unit 40 is implemented by using a CPU, various arithmetic circuits, or the like. The control unit 40 reads information that is memorized or stored in the storage unit 41 from the storage unit 41, and integrally controls the ultrasound imaging device 3 by performing various kinds of arithmetic processing related to an operation method of the ultrasound imaging device 3. Meanwhile, the control unit 40 may be configured using a CPU or the like that is common to the signal processing unit 32, the image generation unit 33, the region setting unit 34, the boundary detection unit 35, the luminance value conversion unit 36, the 3D image generation unit 37, the distance calculation unit 38, the display control unit 39, and the like.

The storage unit 41 stores therein various programs for causing the ultrasound imaging system 1 to perform processing, data including various parameters and the like needed for the processing performed by the ultrasound imaging system 1, and the like. The storage unit 41 stores therein, for example, an initial position (sound-ray number) of a writing start position of the ultrasound image (a transmission start position of an ultrasound wave).

Further, the storage unit 41 stores therein various programs including an operation program for executing the operation method of the ultrasound imaging system 1. The operation program may be widely distributed by being stored in a computer-readable storage medium, such as a hard disk, a flash memory, a compact disc-read only memory (CD-ROM), a digital versatile disk (DVD)-ROM, or a flexible disk. Meanwhile, the various programs as described above may be acquired by download via a communication network. The communication network described herein is implemented by, for example, an existing public line network, a local area network (LAN), a wide area network (WAN), or the like regardless of whether it is a wired or wireless.

The storage unit 41 configured as described above is implemented by using a ROM in which various programs and the like are installed in advance, a random access memory (RAM) in which arithmetic parameters, data, and the like of each of processes are stored, or the like.

The display device 4 is connected to the ultrasound imaging device 3. The display device 4 is configured with a display panel made of liquid crystal, organic electro luminescence (EL), or the like. The display device 4 displays, for example, the ultrasound image output by the ultrasound imaging device 3 and various kinds of information on operation.

Figure 2:
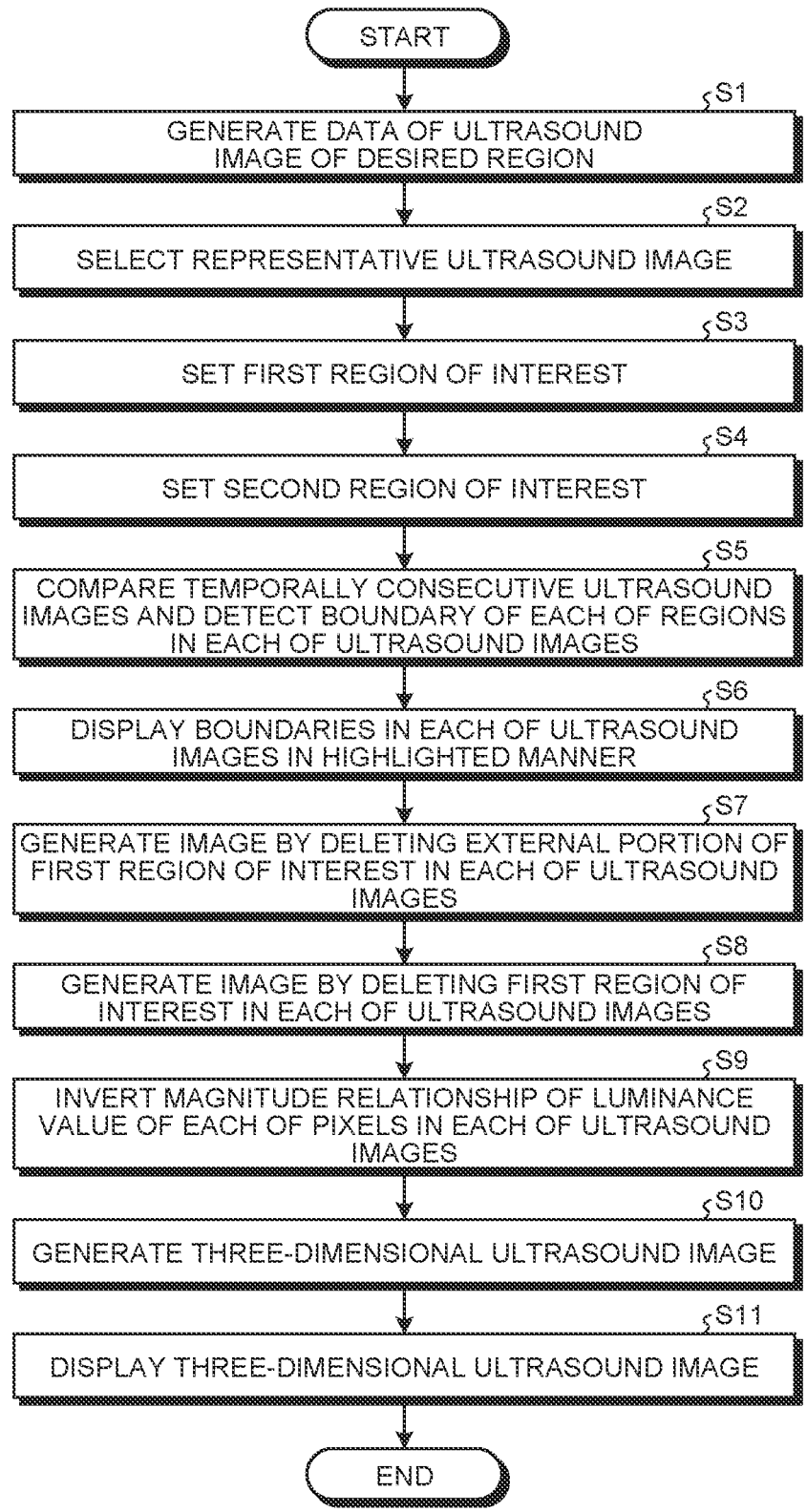
FIG. 2 is a flowchart illustrating a process performed by the ultrasound imaging system illustrated in FIG. 1.
Figure 3:
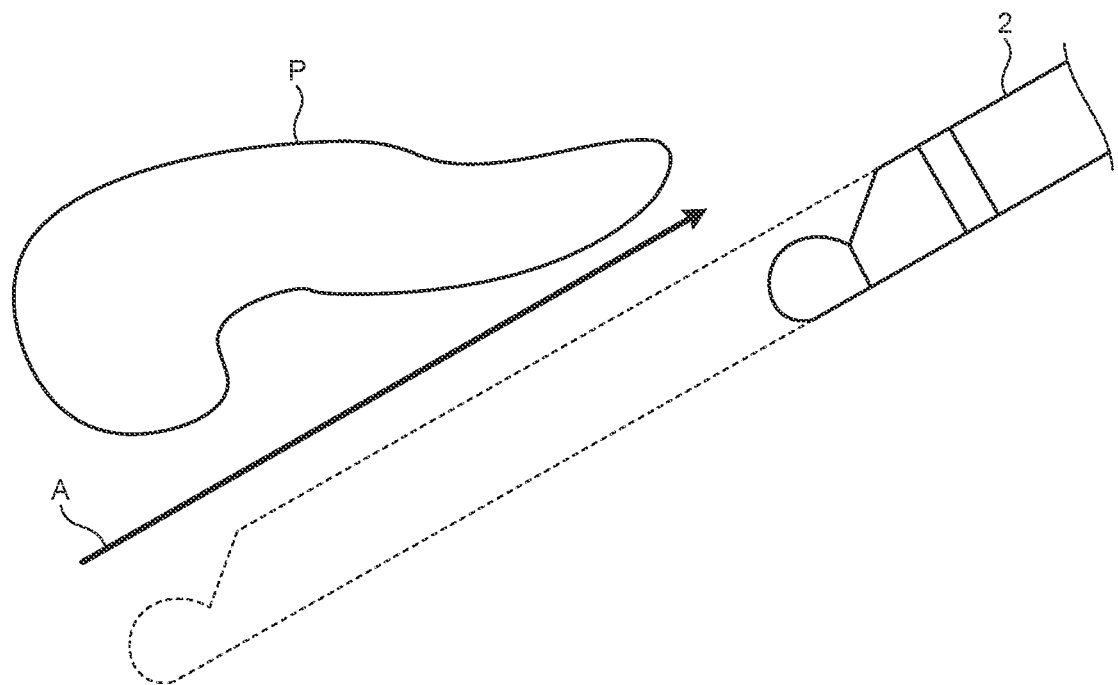
FIG. 3 is a diagram illustrating how to obtain an ultrasound image of a predetermined region.
Figure 4:
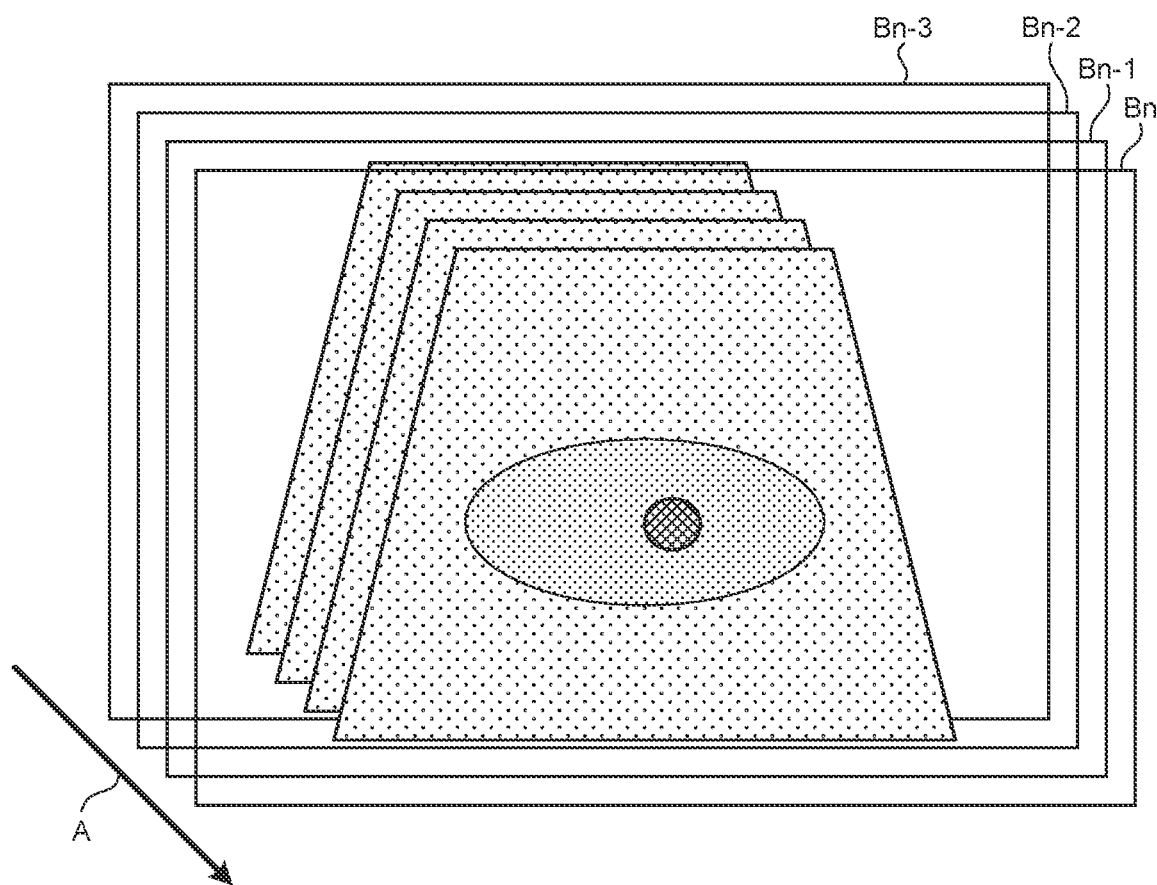
FIG. 4 is a diagram illustrating a generated ultrasound image group.

A process performed by the ultrasound imaging system 1 will be described in detail below. FIG. 2 is a flowchart illustrating the process performed by the ultrasound imaging system illustrated in FIG. 1. As illustrated in FIG. 2, the image generation unit 33 generates data of an ultrasound image of a desired region (Step S1). FIG. 3 is a diagram illustrating how to obtain an ultrasound image of a predetermined region. As illustrated in FIG. 3, the insertion portion of the ultrasound endoscope 2 is moved along a longitudinal direction A and obtains an ultrasound image of a region including a pancreas P. Meanwhile, the insertion portion of the ultrasound endoscope 2 may be manually moved, but it may be possible to mechanically or electronically cause the ultrasound transducer 21 to perform scanning helically. With the movement of the insertion portion of the ultrasound endoscope 2, the image generation unit 33 sequentially generates ultrasound images that are images of cross sections perpendicular to the direction A, and generates data of the ultrasound image group including the pancreas P. FIG. 4 is a diagram illustrating the generated ultrasound image group. As illustrated in FIG. 4, ultrasound images Bn-3, Bn-2, Bn-1, and Bn are sequentially generated along the direction A in which the insertion portion of the ultrasound endoscope 2 is moved. The generated data of the ultrasound image group including the ultrasound images Bn-3, Bn-2, Bn-1, and Bn is sequentially stored in the storage unit 41.

Figure 5:
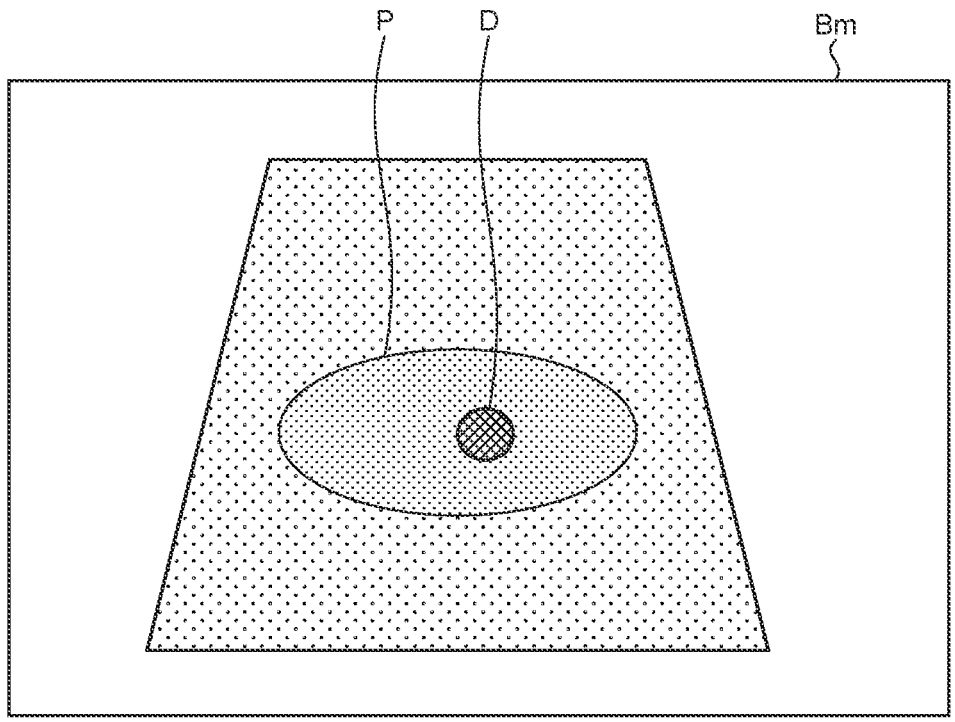
FIG. 5 is a diagram illustrating an example of a selected representative ultrasound image.

If the data of the ultrasound image group is generated, the user selects a representative ultrasound image from the ultrasound image group (Step S2). Specifically, if a pancreas is to be observed for example, the user observes the ultrasound image group displayed on the display device 4, and selects, as the representative ultrasound image, an ultrasound image in which the pancreas or a pancreatic duct appears clearly. FIG. 5 is a diagram illustrating an example of the selected representative ultrasound image. As illustrated in FIG. 5, it is assumed that an ultrasound image Bm that is an m-th ultrasound image is selected as a representative image. The ultrasound image Bm includes, for example, the pancreas P and a pancreatic duct D.

Figure 6:
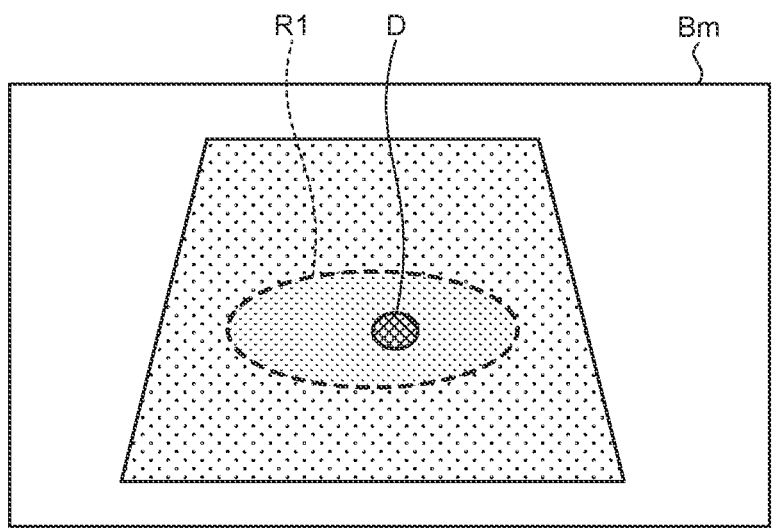
FIG. 6 is a diagram illustrating a state in which a first region of interest is set.

The region setting unit 34 sets the first region of interest in the selected ultrasound image Bm (Step S3). FIG. 6 is a diagram illustrating a state in which the first region of interest is set. As illustrated in FIG. 6, the user sets a first region of interest R1 in the ultrasound image Bm. Specifically, the user selects a pixel included in a region that is to be set as the first region of interest, and, the region setting unit 34 automatically detects a boundary across which a luminance value in the region including the pixel selected by the user changes by a predetermined amount, and sets the first region of interest R1. The region setting unit 34 may automatically detect a boundary across which the luminance value in the region including the pixel selected by the user is largely changed. Meanwhile, the user performs input using an input device, such as a mouse, a track ball, or a touch pad. Further, the user may select a region that is to be set as the first region of interest, and, the region setting unit 34 may automatically detect a boundary across which the luminance value is largely changed with respect to an average value of luminance values of the region set by the user, correct the region selected by the user, and set the first region of interest R1. Meanwhile, the region setting unit 34 may automatically set a region corresponding to the pancreas P as the first region of interest R1 by using an automatic learning function, for example. Furthermore, the region setting unit 34 may have a function to store, when the user corrects the automatically set region, the correction and reflect the correction in next region setting.

Figure 7:
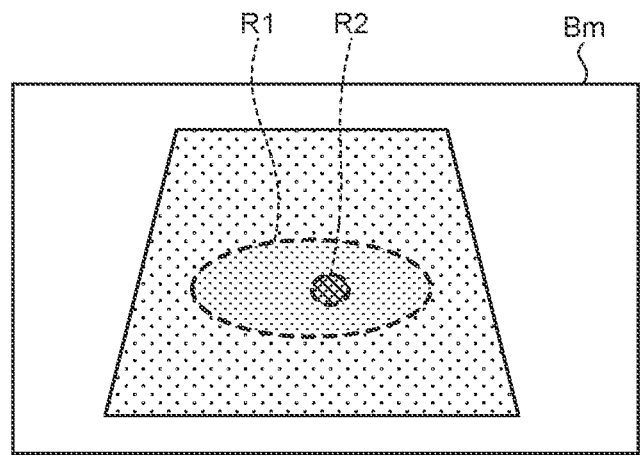
FIG. 7 is a diagram illustrating a state in which a second region of interest is set.
Figure 8:
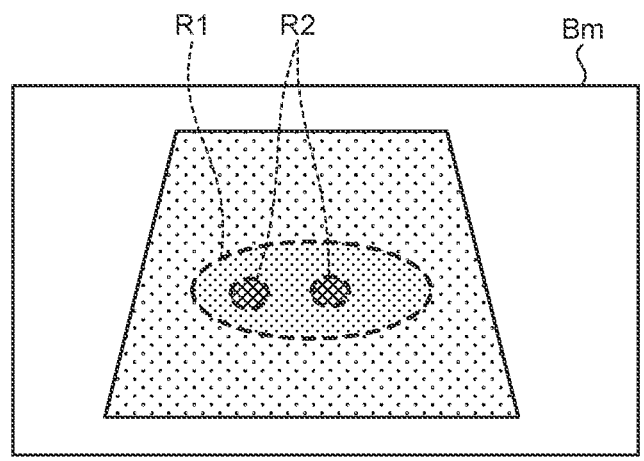
FIG. 8 is a diagram illustrating a state in which the second regions of interest are set.

Subsequently, the region setting unit 34 sets a second region of interest (Step S4). FIG. 7 and FIG. 8 are diagrams illustrating states in which the second region of interest is set. As illustrated in FIG. 7, the user sets a second region of interest R2 in the ultrasound image Bm. Specifically, the user selects a pixel included in a region that is to be set as the second region of interest, and, the region setting unit 34 automatically detects a boundary across which a luminance value in the region including the pixel selected by the user changes by a predetermined amount, and sets the second region of interest R2. The region setting unit 34 may automatically detects a boundary across which a luminance value in the region including the pixel selected by the user is largely changed. Further, the user may select a region that is to be set as the second region of interest, and, the region setting unit 34 may automatically detect a boundary across which the luminance value is largely changed with respect to an average value of luminance values of the region set by the user, correct the region selected by the user, and set the second region of interest R2. Meanwhile, as illustrated in FIG. 8, if the ultrasound image Bm includes two regions such as a region corresponding to the pancreatic duct D and a region corresponding to the pustule, the user may set each of the two regions as the second region of interest R2. Furthermore, the region setting unit 34 may automatically set the region corresponding to the pancreatic duct D and the region corresponding to the pustule as the second regions of interest R2 by using the automatic learning function, for example. Moreover, the region setting unit 34 may have a function to store, when the user corrects the automatically set second region of interest R2, the correction and reflect the correction in next region setting.

The boundary detection unit 35 compares temporally consecutive ultrasound images and detects a boundary of each of the regions in each of the ultrasound images (Step S5). Specifically, the boundary detection unit 35 sequentially compares temporally consecutive ultrasound images from among ultrasound images obtained before and after the selected ultrasound image Bm, and detects a boundary between the first region of interest R1 and an external portion of the first region of interest R1 and a boundary between the first region of interest R1 and the second region of interest R2 in each of the ultrasound images. Meanwhile, the boundary detection unit 35 may detect the boundaries by using the automatic learning function. Furthermore, the boundary detection unit 35 may have a function to store, when the user corrects the automatically detected boundaries, the correction and reflect the correction in next boundary detection.

Figure 9:
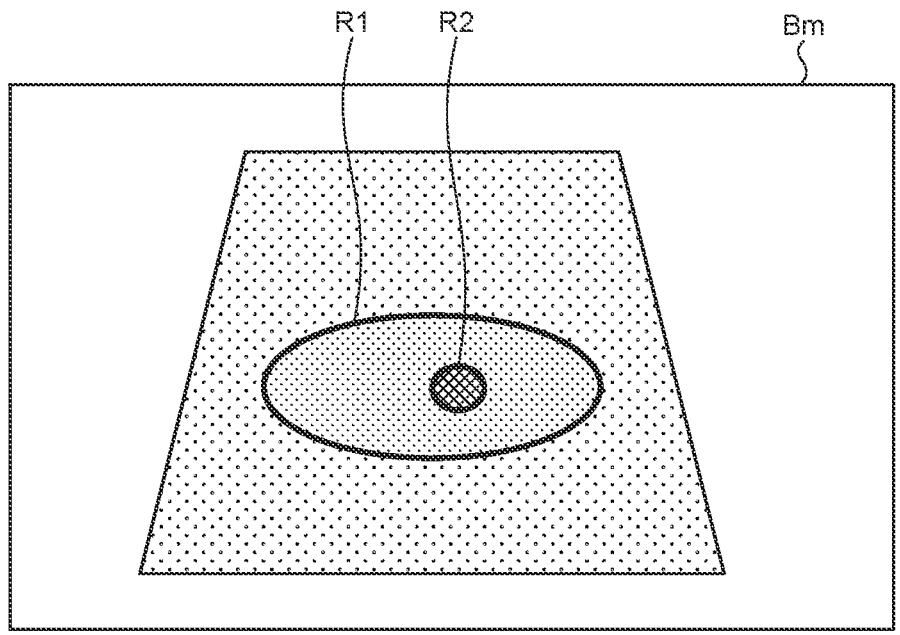
FIG. 9 is a diagram illustrating as state in which each of boundaries is displayed in a highlighted manner.

The display control unit 39 causes the display device 4 to display the boundaries in each of the ultrasound images in a highlighted manner (Step S6). Specifically, the display control unit 39 causes the display device 4 to display the boundary between the first region of interest R1 and the external portion of the first region of interest R1 and the boundary between the first region of interest R1 and the second region of interest R2, which are detected by the boundary detection unit 35, in a highlighted manner in each of the ultrasound images. FIG. 9 is a diagram illustrating a state in which each of the boundaries is displayed in a highlighted manner. As illustrated in FIG. 9, the display control unit 39 causes the display device 4 to display the boundary between the first region of interest R1 and the external portion of the first region of interest R1 and the boundary between the first region of interest R1 and the second region of interest R2, which are detected by the boundary detection unit 35, in a highlighted manner by changing widths of lines, types of the lines, colors, or the like in each of the ultrasound images.

Figure 10:
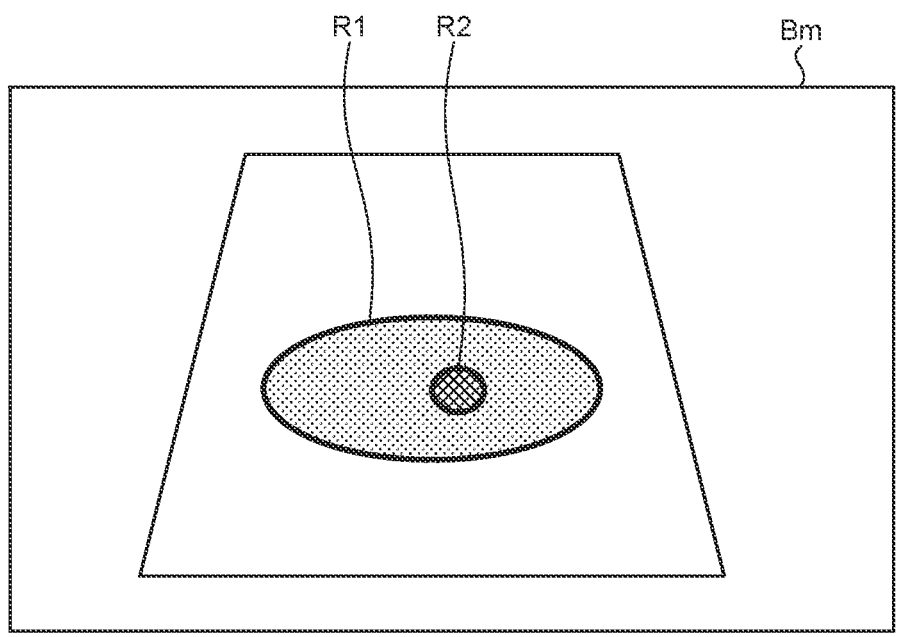
FIG. 10 is a diagram illustrating a state in which an external portion of the first region of interest is deleted.
Figure 11:
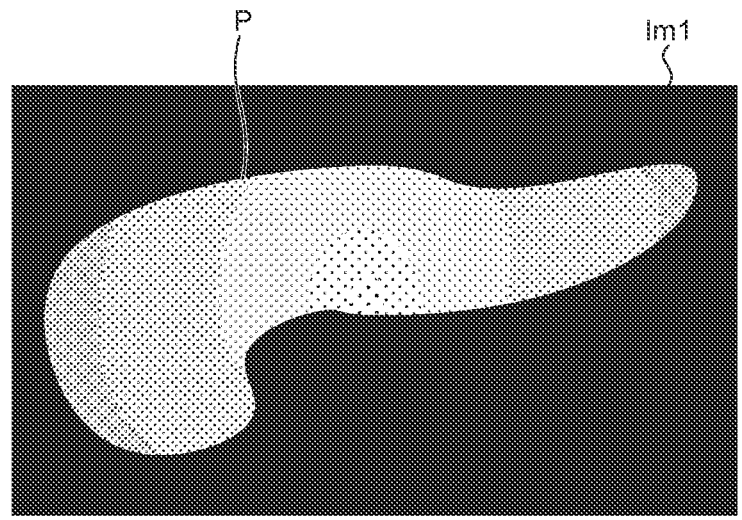
FIG. 11 is a diagram illustrating one example of a three-dimensional ultrasound image.

The image generation unit 33 generates an image by deleting the external portion of the first region of interest R1 in each of the ultrasound images (Step S7). FIG. 10 is a diagram illustrating a state in which the external portion of the first region of interest is deleted. As illustrated in FIG. 10, the image generation unit 33 generates an image by deleting the external portion of the first region of interest R1 and retaining only a target organ, such as the pancreas, in each of the ultrasound images. As a result, it is possible to easily observe the target organ. Meanwhile, the 3D image generation unit 37 may generate a three-dimensional ultrasound image by synthesizing images in each of which the external portion of the first region of interest R1 of each of the ultrasound image is deleted. FIG. 11 is a diagram illustrating one example of the three-dimensional ultrasound image. As illustrated in FIG. 11, it is possible to observe a shape of the target organ, such as the pancreas P, by using a three-dimensional ultrasound image Im1.

Figure 12:
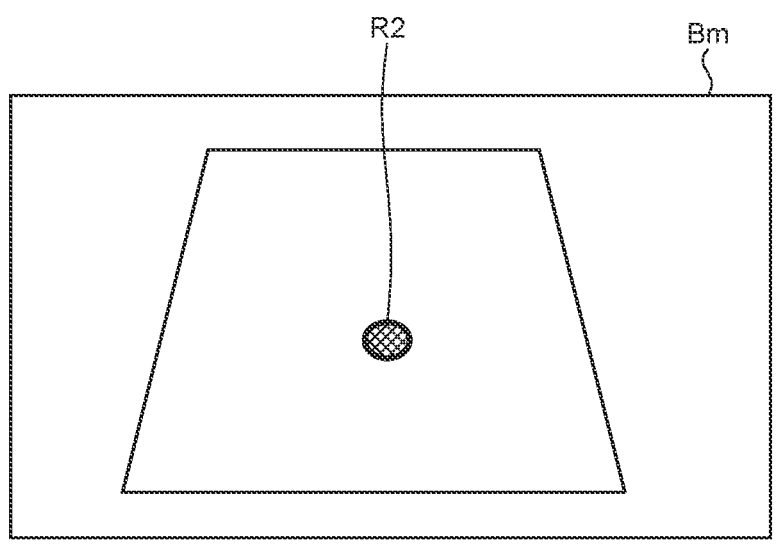
FIG. 12 is a diagram illustrating a state in which the first region of interest is deleted.
Figure 13:
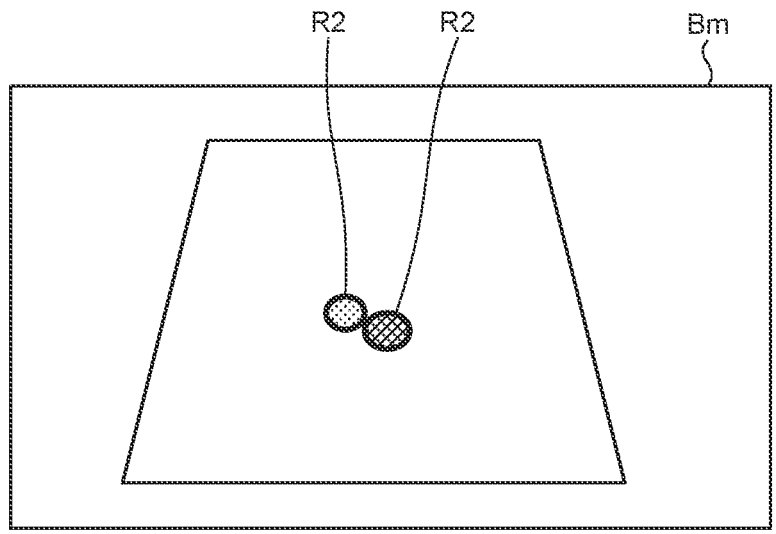
FIG. 13 is a diagram illustrating a state in which the first region of interest is deleted.

The image generation unit 33 generates an image by deleting the first region of interest R1 in each of the ultrasound images (Step S8). FIG. 12 and FIG. 13 are diagrams illustrating states in which the first region of interest is deleted. As illustrated in FIG. 12, the image generation unit 33 generates an image by deleting the first region of interest R1 and retaining only an observation target, such as the pancreatic duct D, in each of the ultrasound images. As a result, it is possible to easily observe the observation object. Furthermore, as illustrated in FIG. 8, if the region corresponding to the pustule is set as the second region of interest R2, as illustrated in FIG. 13, the image generation unit 33 generates an image by deleting the first region of interest R1 and retaining only an observation target including the pancreatic duct D and the pustule in each of the ultrasound images.

Figure 14:
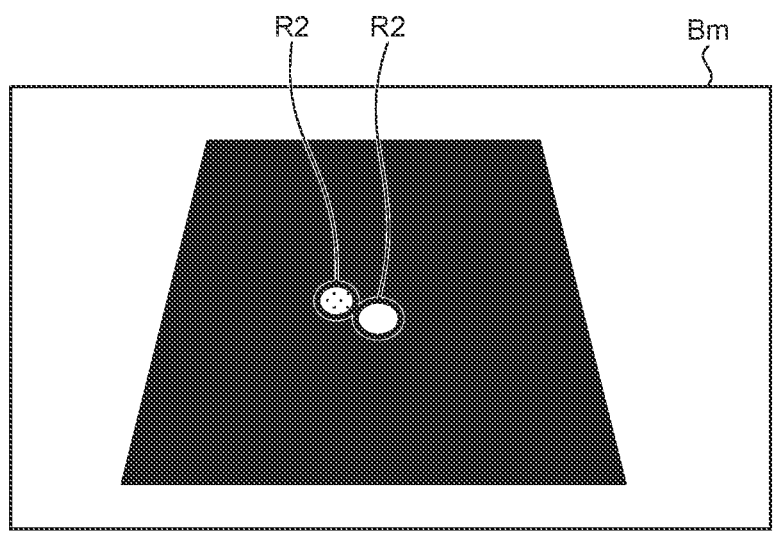
FIG. 14 is a diagram illustrating a state in which a magnitude relationship of a luminance value is inverted.

The luminance value conversion unit 36 inverts the magnitude relationship of the luminance value of each of the pixels in the ultrasound image (Step S9). FIG. 14 is a diagram illustrating a state in which the magnitude relationship of the luminance value is inverted. As illustrated in FIG. 14, the luminance value conversion unit 36 performs negative-to-positive conversion for inverting the magnitude relationship of the luminance value on each of the pixels in the ultrasound image. As a result, it is possible to easily observe a region that corresponds to the pancreatic duct D and the pustule, that naturally have low luminance values, and that are not easily viewable.

Figure 15:
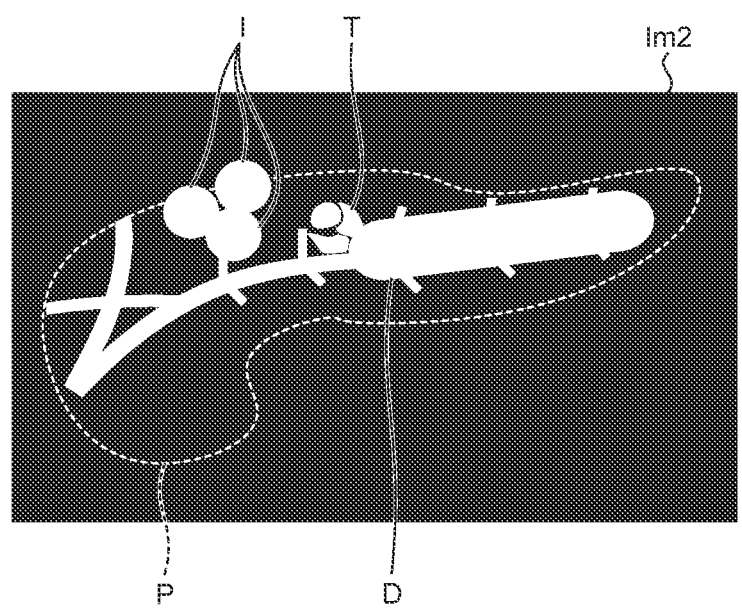
FIG. 15 is a diagram illustrating an example of a three-dimensional ultrasound image in which luminance values are inverted.

The 3D image generation unit 37 generates a three-dimensional ultrasound image by synthesizing the ultrasound images (Step S10). FIG. 15 is a diagram illustrating an example of the three-dimensional ultrasound image in which luminance values are inverted. As illustrated in FIG. 15, a three-dimensional ultrasound image Im2 includes the pancreatic duct D, a pustule T, and a neoplastic pancreatic pustule I.

Further, the display control unit 39 causes the display device 4 to display the three-dimensional ultrasound image (Step S11).

As described above, according to one embodiment, it is possible to more easily observe the observation object, such as the pancreatic duct D, the pustule T, or the neoplastic pancreatic pustule I.

In the ultrasound image, the pancreatic duct D, the pustule T, the neoplastic pancreatic pustule I, and the like naturally have low luminance values and are not easily observable; however, in the ultrasound imaging system 1, the negative-to-positive conversion is performed, so that the observation objects can easily be observed. Furthermore, in the conventional ultrasound imaging system, it is only possible to observe an outer surface of the pancreas P as in the three-dimensional ultrasound image Im1 illustrated in FIG. 11; however, in the ultrasound imaging system 1, the external portion of the first region of interest R1 and the first region of interest R1 are deleted, so that it is possible to observe the pancreatic duct D, the pustule T, and the neoplastic pancreatic pustule I as in the three-dimensional ultrasound image Im2 illustrated in FIG. 15. Meanwhile, as illustrated in FIG. 15, the pancreas P that serves as the boundary between the first region of interest R1 and the external portion may be displayed by a dashed line or the like. By observation of FIG. 15, it is possible to easily and visually confirm that main pancreatic duct expansion has occurred on the right side of the pustule because the pancreatic duct D is compressed by the pustule T.

Meanwhile, in the flowchart as described above, the example has been described in which the external portion of the first region of interest R1 is first deleted, the first region of interest R1 is subsequently deleted, and the negative-to-positive conversion is finally performed, but the order of processes is not limited to this example. For example, it may be possible to first perform the negative-to-positive conversion, and thereafter delete the external portion of the first region of interest R1 and the first region of interest R1 by discarding a portion in which a luminance value in the converted image is equal to or smaller than a threshold. In this case, it is not necessary to detect the boundary between the first region of interest R1 and the external portion of the first region of interest R1 and the boundary between the first region of interest R1 and the second region of interest R2.

Meanwhile, in the embodiment as described above, the example has been described in which the luminance value conversion unit 36 inverts the magnitude relationship of the luminance value and thereafter set a luminance value equal to or smaller than the threshold to zero, but embodiments are not limited to this example. The luminance value conversion unit 36 may invert the magnitude relationship of the luminance value and thereafter set a luminance value equal to or smaller than the threshold to an adequately small predetermined value such that a corresponding portion can have a transparency and an internal structure can be viewed. In this case, it is possible to view the shape of the pancreas P and also view the observation object, such as the pancreatic duct D, the pustule T, or the neoplastic pancreatic pustule I.

Furthermore, the ultrasound endoscope may be configured using a miniature probe that can be inserted into a treatment tool channel of an endoscope.

According to the present disclosure, it is possible to realize the ultrasound imaging system capable of easily observing an observation object.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound imaging system comprising:
a processor comprising hardware, the processor being configured to:
generate data of an ultrasound image of a subject;
set a first boundary in the ultrasound image across which luminance values of pixels in the ultrasound image changes by a predetermined amount, the first boundary representing a boundary between a first portion of the subject and an external portion external of the first boundary;
set, based on the first boundary set, a second boundary from within the first boundary in the ultrasound image, the second boundary representing a boundary between the first portion of the subject external of the second boundary and a second portion of the subject internal of the second boundary;

delete a region between the first boundary and the second boundary; and after deleting the region between the first boundary and the second boundary, invert a magnitude relationship of a luminance value of each pixel in the ultrasound image.

2. The ultrasound imaging system according to claim 1, wherein the ultrasound image is a first ultrasound image, and wherein the processor is further configured to:

generate data of a second ultrasound image of the subject;

set a first boundary in the second ultrasound image across which luminance values of pixels in the second ultrasound image changes by the predetermined amount, the first boundary in the second ultrasound image representing a boundary between the first portion of the subject and an external portion external of the first boundary in the second ultrasound image;

set, based on the first boundary in the second ultrasound image set, a second boundary in the second ultrasound image from within the first boundary in the second ultrasound image, the second boundary in the second ultrasound image representing a boundary between the first portion of the subject external of the second boundary in the second ultrasound image and the second portion of the subject internal of the second boundary in the second ultrasound image;

delete a region between the first boundary and the second boundary of the second ultrasound image;

after deleting the region between the first boundary and the second boundary of the second ultrasound image, invert a magnitude relationship of a luminance value of each pixel in the second ultrasound image; and generate data of a three-dimensional ultrasound image by synthesizing the first ultrasound image and the second ultrasound image after performing inversion of the magnitude relationships in the first ultrasound image and the second ultrasound image.

3. The ultrasound imaging system according to claim 2, wherein the processor is further configured to generate data of a two-dimensional cross-sectional image of an arbitrary cross-section in the three-dimensional ultrasound image.

4. The ultrasound imaging system according to claim 2, wherein the processor is further configured to cause a display to display:

the first ultrasound image and the second ultrasound image; and the three-dimensional ultrasound image.

5. The ultrasound imaging system according to claim 1, wherein the processor is further configured to:

cause a display to display an image of the subject based on the ultrasound image generated; and calculate a distance between two points that are specified in the image of the subject displayed on the display.

6. The ultrasound imaging system according to claim 1, wherein the ultrasound image is a first ultrasound image of a first section of the subject, and wherein the processor is configured to generate data of a second ultrasound image of a second section the subject, the first section of the subject being spatially separated from the second section of the subject in a predetermined direction.

7. The ultrasound imaging system according to claim 1, wherein the processor is further configured to generate an image in which the external portion is deleted.

8. The ultrasound imaging system according to claim 1, further comprising:

an ultrasound endoscope comprising:

an insertion portion configured to be inserted into the subject; and an ultrasound transducer arranged at a distal end of the insertion portion, the ultrasound transducer configured to convert an ultrasound echo reflected by the subject to an ultrasound signal, wherein the processor is configured to generate the data of the ultrasound image based on the ultrasound signal.

9. An operation method of an ultrasound imaging system, the operation method comprising:

generating data of an ultrasound image of a subject;

setting a first boundary in the ultrasound image across which luminance value of pixels in the ultrasound image changes by a predetermined amount, the first boundary representing a boundary between a first portion of the subject and an external portion external of the first boundary;

setting, based on the first boundary set, a second boundary from within the first boundary in the ultrasound image, the second boundary representing a boundary between the first portion of the subject external of the second boundary and a second portion of the subject internal of the second boundary;

deleting a region between the first boundary and the second boundary; and after deleting the region between the first boundary and the second boundary, inverting a magnitude relationship of a luminance value of each pixel in the ultrasound image.

10. The operation method according to claim 9, wherein the ultrasound image is a first ultrasound image, and wherein the operation method further comprises:

generating data of a second ultrasound image of the subject;

setting a first boundary in the second ultrasound image across which luminance values of pixels in the second ultrasound image changes by the predetermined amount, the first boundary in the second ultrasound image representing a boundary between the first portion of the subject and an external portion external of the first boundary in the second ultrasound image;

setting, based on the first boundary in the second ultrasound image set, a second boundary in the second ultrasound image from within the first boundary in the second ultrasound image, the second boundary in the second ultrasound image representing a boundary between the first portion of the subject external of the second boundary in the second ultrasound image and the second portion of the subject internal of the second boundary in the second ultrasound image;

deleting a region between the first boundary and the second boundary of the second ultrasound image;

after deleting the region between the first boundary and the second boundary of the second ultrasound image, inverting a magnitude relationship of a luminance value of each pixel in the second ultrasound image; and generating data of a three-dimensional ultrasound image by synthesizing the first ultrasound image and the second ultrasound image after performing inversion of the magnitude relationships in the first ultrasound image and the second ultrasound image.

11. The operation method according to claim 10, further comprising:

generating data of a two-dimensional cross-sectional image of an arbitrary cross-section in the three-dimensional ultrasound image.

12. The operation method according to claim 10, further comprising:

causing a display to display:
the first ultrasound image and the second ultrasound image; and
the three-dimensional ultrasound image.

13. The operation method according to claim 9, further comprising:

causing a display to display an image of the subject based on the ultrasound image generated; and
calculate a distance between two points that are specified in the image of the subject displayed on the display.

14. The operation method according to claim 9,
wherein the ultrasound image is a first ultrasound image of a first section of the subject, and
wherein the operation method further comprises generating data of a second ultrasound image of a second section the subject, the first section of the subject being spatially separated from the second section of the subject in a predetermined direction.

15. The operation method according to claim 9, further comprising:

generating an image in which the external portion is deleted.

16. An ultrasound imaging system comprising:
a processor comprising hardware, the processor configured to:
generate data of an ultrasound image of a subject;
set a first boundary in the ultrasound image across which luminance values of pixels in the ultrasound image changes by a predetermined amount, the first boundary being a first outline of a first portion of the subject;
set, based on the first boundary set, a second boundary from within the first boundary in the ultrasound image, the second boundary being a second outline of a second portion of the subject, the second boundary being located inside the first boundary;
delete a region between the first boundary and the second boundary; and
after deleting the region between the first boundary and the second boundary, invert a magnitude relationship of a luminance value of each pixel in the ultrasound image.

17. The ultrasound imaging system according to claim 16, wherein the ultrasound image is a first ultrasound image, and
wherein the processor is further configured to:
generate data of a second ultrasound image of the subject;
set a first boundary in the second ultrasound image across which luminance values of pixels in the second ultrasound image changes by the predetermined amount, the first boundary in the second ultrasound image, the first boundary in the second ultrasound image being a first outline of a first portion of the subject in the second ultrasound image;
set, based on the first boundary in the second ultrasound image set, a second boundary in the second ultrasound image from within the first boundary in the second ultrasound image, the second boundary in the second ultrasound image being a second outline of a second portion of the subject in the second ultrasound image, the second boundary in the second ultrasound image located inside the first boundary;
delete a region between the first boundary and the second boundary of the second ultrasound image;
after deleting the region between the first boundary and the second boundary of the second ultrasound image, invert a magnitude relationship of a luminance value of each pixel in the second ultrasound image; and
generate data of a three-dimensional ultrasound image by synthesizing the first ultrasound image and the second ultrasound image after performing inversion of the magnitude relationships in the first ultrasound image and the second ultrasound image.

18. The ultrasound imaging system according to claim 17, further comprising:

generating data of a two-dimensional cross-sectional image of an arbitrary cross-section in the three-dimensional ultrasound image.

19. The ultrasound imaging system according to claim 17, further comprising:

causing a display to display:
the first ultrasound image and the second ultrasound image; and
the three-dimensional ultrasound image.

* * * * *